(12) United States Patent
Zimmermann et al.

(10) Patent No.: US 7,244,931 B2
(45) Date of Patent: Jul. 17, 2007

(54) ION MOBILITY SPECTROMETER WITH PARALLEL RUNNING DRIFT GAS AND ION CARRIER GAS FLOWS

(75) Inventors: Stefan Zimmermann, Lübeck (DE); Wolfgang Bäther, Lübeck (DE)

(73) Assignee: Dräger Safety AG & Co. KGAA (DE)

( * ) Notice: Subject to any disclaimer, the term of this patent is extended or adjusted under 35 U.S.C. 154(b) by 8 days.

(21) Appl. No.: 11/280,868

(22) Filed: Nov. 16, 2005

(65) Prior Publication Data

US 2006/0186330 A1    Aug. 24, 2006

(30) Foreign Application Priority Data

Feb. 18, 2005  (DE)  .................. 10 2005 007 746

(51) Int. Cl.
*H01J 49/40* (2006.01)
(52) U.S. Cl. .................. 250/292; 250/287; 250/288; 250/293; 250/294
(58) Field of Classification Search .................. None
See application file for complete search history.

(56) References Cited

U.S. PATENT DOCUMENTS

| | | | |
|---|---|---|---|
| 3,835,328 A | 9/1974 | Harris et al. | |
| 3,870,888 A | 3/1975 | Lovelock | |
| 4,075,550 A | 2/1978 | Castleman et al. | |
| 4,777,363 A | 10/1988 | Eiceman et al. | |
| 5,047,723 A | 9/1991 | Puumalainen | |
| 5,223,712 A | 6/1993 | Adams et al. | |
| 5,420,424 A * | 5/1995 | Carnahan et al. | 250/287 |
| 6,495,823 B1 * | 12/2002 | Miller et al. | 250/286 |
| 6,621,077 B1 * | 9/2003 | Guevremont et al. | 250/292 |
| 6,690,004 B2 * | 2/2004 | Miller et al. | 250/286 |
| 6,787,765 B2 * | 9/2004 | Guevremont et al. | 250/288 |
| 7,005,633 B2 * | 2/2006 | Guevremont et al. | 250/287 |
| 7,164,124 B2 * | 1/2007 | Takada et al. | 250/288 |
| 2003/0155503 A1 | 8/2003 | Murphy et al. | |

FOREIGN PATENT DOCUMENTS

WO    WO 94/16320    7/1994

OTHER PUBLICATIONS

Spangler et al., 1983, *Membrane Inlet for Ion Mobility Spectrometry (Plasma Chromatography)*, International Journal of Mass Spectrometry and Ion Physics, 52 (1983) 267-287.

* cited by examiner

*Primary Examiner*—David A. Vanore
(74) *Attorney, Agent, or Firm*—McGlew and Tuttle, PC

(57) ABSTRACT

An ion mobility spectrometer is provided including at least one ionization chamber (1), which can be passed through by analyte-containing gas and at least one radiation source (2), from which ionizing radiation which is suitable for at least partially ionizing the analyte-containing gas enters the ionization chamber (1). At least one transition area (3) is provided, into which the at least partially ionized gas as ion carrier gas (4) and an almost ion-free gas as drift gas (5) can be charged in a way that, at least at the end of the transition area (3), a flow is established, in which cross-sectional areas (6) are mainly passed through by ion carrier gas (4) and other cross-sectional areas (7, 7') are mainly passed through by drift gas (5). At least one separation area (8) is provided lying in the direction of flow behind the transition area (3), in which, likewise, cross-sectional areas are mainly passed through by ion carrier gas (4) and other cross-sectional areas are mainly passed through by drift gas (5). The drift gas (5) and ion carrier gas (4) flow unidirectionally, and the cross-sectional areas (6) that are mainly passed through by ion carrier gas (4) are smaller at least in one dimension than the cross-sectional areas (7, 7') that are mainly passed through by drift gas (5).

41 Claims, 4 Drawing Sheets

ION MOBILITY SPECTROMETER WITH PARALLEL RUNNING DRIFT GAS AND ION CARRIER GAS FLOWS

CROSS REFERENCE TO RELATED APPLICATIONS

This application claims the benefit of priority under 35 U.S.C. § 119 of German Patent Application DE 10 2005 007 746.3 filed Feb. 18, 2005, the entire contents of which are incorporated herein by reference.

FIELD OF THE INVENTION

The present invention pertains to an ion mobility spectrometer with parallel running drift gas and ion carrier gas flows.

BACKGROUND OF THE INVENTION

Ion mobility spectrometers (IMS) are used for detecting trace substances in the air. They are widely used particularly in the detection of explosives, illegal drugs, chemical weapons and toxic industrial gases. The characteristic structural components of an ion mobility spectrometer are ionization chambers, drift chambers and detectors. The ionization chamber and the drift chamber in conventional ion mobility spectrometers are usually separated by a grid. In the ionization chamber, the analyte molecules to be determined are converted into ions. The ions formed are transferred from the ionization chamber to the drift chamber as an ion swarm due to the effect of an electric field. Under the effect of an electric high voltage field, the analyte ions pass through the drift chamber against the resistance of the drift gas and are, partly due to a different mobility of various ions, detected by the detector in a time-resolved manner, because different analyte ions display different interactions with the drift gas, therefore have different flight times and may thus be separated from one another.

Ion mobility spectrometers have become known, in which the drift gas flows from the detector in the direction of the ionization chamber. The analyte gas is ionized and flows within the ionization chamber in the direction of a grid. The ions formed thus move with the analyte gas in the direction of the grid and then up to the detector under the effect of a high voltage field against the direction of flow of the drift gas (Spangler and Carrico, *Int. J. Mass Spectrom. Ion Phys.*, 1983, 52, 627).

A unidirectional flow guide, in which the analyte gas is fed into the device on the detector side and leaves the device again on the ionization chamber side, is described by Eiceman in U.S. Pat. No. 4,777,363. The ionization takes place in the ionization chamber, and the ions are accelerated against the flow of analyte gas up to the detector. Drift gas and analyte gas are identical here.

Both systems require a homogeneous electric field within the drift chamber for the separation of the ions. This homogeneous electric field is composed from a series of annular electrodes, each of which is electrically insulated. The necessary high voltage is usually 2,000–3,000 V. Such systems are very expensive, complicated to manufacture and are miniaturized only with difficulty.

Furthermore, unlike the IMS described above, it has become known how to guide the ions to be separated unidirectionally with the drift gas flow. The ions can be deflected out of this direction of flow by a relatively low voltage. Once they have then reached electrodes, which are formed by the walls, they can be discharged, and a flow can be measured. Drift gas and analyte gas are identical here.

Such a system is found in so-called electron capture detectors. Lovelock discloses an early example in U.S. Pat. No. 3,870,888. Total ion flows can be measured with such systems. On the other hand, making a distinction between individual types of ions is not possible.

It has become known how to separate long-lived ions from short-lived ions by means of extending the drift sections, e.g., by incorporating flow spoilers. This principle is described, for example, in the detection of chemical weapons (U.S. Pat. Nos. 3,835,328, US 4,075,550, as well as US 5,223,712). The separation efficiency of systems of this type is relatively poor, which may relatively frequently lead to the triggering of a false alarm.

A variant is described by Puumalainen in U.S. Pat. No. 5,047,723. In this case, the gas flow to be analyzed is first ionized and then guided by a series of electric deflecting fields. Depending on the type of the ions, these are each discharged to different electrodes. The flow is measured and is an indicator of the analytes present.

In WO 9416320 Paakanen et al. further modified a system of this type and identify substances based on the characteristic patterns that result from a plurality of electrodes closely connected in series by means of the discharge of ions. Besides ion signals, signals of semiconductor sensors were also included in a pattern recognition.

Furthermore, it has become known how to improve the last-mentioned system by the analyte gas being heated before the analysis and by the sensor electrodes forming multidimensional arrays (US 2003/0155503 A1). In this case as well, the evaluation of signals is based on a pattern recognition. Connected to this is the drawback that the measuring system must first learn the respective pattern, thus an extremely high calibrating expense is necessary. This applies particularly in mixtures. Not considered mixtures, i.e., for example, combinations of analytes to be monitored with unknown impurities, may lead to false alarms or may prevent the detection of the analytes to be monitored.

Finally, it has become known to deflect the analyte ions by means of a high-frequency alternating field, on which is superimposed a low compensating voltage. Here, the analyte ions are transported in a system likewise in the direction of the drift gas (U.S. Pat. No. 6,495,823). A defined kind of analyte ion is allowed through the system and reaches the detector only under the defined conditions of the alternating field and of the compensating voltage. These ion sensors, which can be manufactured structurally small, can be joined together into arrays. Systems of this type are, however, expensive and extremely susceptible to environmental influences, such as pressure and humidity.

SUMMARY OF THE INVENTION

The object of the present invention is to provide an ion mobility spectrometer that can be produced in a cost-favorable manner, is insensitive to fluctuations of environmental conditions, in particular ambient humidity, has a good separation efficiency with high recognition reliability and is suitable for miniaturization according to its working principle.

The present invention is based on a concentration of analyte ions to be detected in a certain cross-sectional area of the entry zone of a passed-through separation area. This is achieved by charging in an ion-containing ion carrier gas and an almost ion-free drift gas according to the present invention. The charging in takes place in such a way that the ion carrier gas and the drift gas move through the separation area in the form of a preferably laminar flow in parallel to one another, without considerably blending. Because of the slight blending of the flowing gases, the desired concentration of the analyte ions to be detected is retained in a certain cross-sectional area, until the ions are exposed to the influence of an electric deflecting field.

The ions are deflected transversely to the direction of flow in the separation area. Since the ions are fed into the separation area only in a certain cross-sectional area all ions that have the same mobility are depicted on a marginal area of the separation area, whose position depends on the flow conditions in the separation area, the strength of the deflecting field, the mobility of the ions and the size and position of the cross-sectional area, in which the ions are fed into the separation area. Ions with a different mobility are deflected to another marginal area. The flow, which is caused by ions of a certain mobility, can be measured by arranging a relatively small detector electrode. This flow is an indicator of the concentration of the ions precisely of this certain mobility. The feeding of the analyte ions and the maintenance of the flow conditions according to the present invention lead to a focusing of the analyte ions on a certain cross-sectional area, from which the ions are extracted by the deflecting field. The focusing of the ions makes other measures for an upwards concentration unnecessary. The focusing according to the present invention is at the same time the prerequisite for an evaluable unmixing of analyte ions having different mobility by an electric deflecting field transversely to the direction of flow.

For characterizing the flow conditions, the designations ion carrier gas and drift gas are retained below, even if a carrier gas completely free of ions possibly flows in the separation area due to the effect of the deflecting field, and the ions are deflected through the drift gas, such that individual volume areas of the drift gas appear to be enriched with ions to a considerable extent in the separation area.

The present invention is embodied by an ion mobility spectrometer, which comprises at least one ionization chamber that can be passed through by analyte-containing gas and at least one radiation source, from which ionizing radiation, which is suitable for at least partially ionizing the analyte-containing gas, enters the ionization chamber.

To the ionization chamber is connected at least one transition area, into which the at least partially ionized gas as ion carrier gas and an almost ion-free gas as drift gas can be charged in a way that at least at the end of the transition area a flow is established, in which cross-sectional areas are mainly passed through by ion carrier gas and other cross-sectional areas are mainly passed through by drift gas.

In the direction of flow behind the transition area is located at least one separation area, in which likewise cross-sectional areas are mainly passed through by ion carrier gas and other cross-sectional areas are mainly passed through by drift gas.

For characterizing the relationships of the cross-sectional areas, the sum of the cross-sectional areas that are passed through by the same type of gas is always intended when using the plural below.

The drift gas and ion carrier gas flow unidirectionally and are not identical. Those cross-sectional areas that are mainly passed through by ion carrier gas are smaller at least in one dimension than the cross-sectional areas that are mainly passed through by drift gas. This results in the focusing of the analyte ions in certain cross-sectional areas according to the present invention. At least one detector electrode, at least one auxiliary electrode and at least one counterelectrode are located in the separation area. These are arranged in such a way that an electric field can be formed between them, which has at least one field component that does not run parallel to the direction of flow in the separation area. In order to be able to utilize the effect of the focusing, it is important for at least one cross-sectional area that is mainly passed through by drift gas to be located between the cross-sectional areas that are mainly passed through by ion carrier gas and the detector electrode.

Unlike most of the IMS according to the state of the art already described, the ions to be separated are guided unidirectionally with the drift gas flow. The ions are deflected out of this direction of flow by a relatively low voltage. Once they have reached the electrodes, which are preferably arranged near the walls of the separation area, they can be discharged, and a flow can be measured.

This principle according to the present invention requires only relatively low deflecting voltages. As a result, the expense for activation and evaluation electronics drops. Miniaturization is likewise easier to achieve.

Thus, low material requirements and low costs will lead to further advantages of arrangements of this type. The design permits a continuous detection of ions and thus a better detection limit.

It is possible to achieve an especially effective focusing of the analyte ions according to the present invention if the cross-sectional areas that are mainly passed through by ion carrier gas are smaller in two dimensions than the cross-sectional areas that are mainly passed through by drift gas. If the focusing is desired only in one dimension, which is sufficient for many applications, then it is advantageous if the cross-sectional areas that are mainly passed through by ion carrier gas have smaller dimensions in the direction of the electric field than the cross-sectional areas that are mainly passed through by drift gas.

A good mobility-dependent unmixing of the analyte ions and thus improved separation efficiency of the IMS according to the present invention, even in miniaturized embodiments, is already obtained if the cross-sectional areas that are mainly passed through by ion carrier gas have an expansion that is smaller by at least a factor of 10 in the direction of the electric field than the cross-sectional areas that are mainly passed through by drift gas. It is especially advantageous if the cross-sectional areas that are mainly passed through by ion carrier gas have an expansion that is smaller by at least a factor of 50 in this direction than cross-sectional areas that are mainly passed through by drift gas.

It has been shown that, aside from the degree of focusing of the analyte ions for the achievable resolution of an IMS according to the present invention, especially the arrangement of the area that is passed through by ion carrier gas is important. Thus, it is advantageous if the transition area and the separation area are designed such that the main part of the cross-sectional areas that are mainly passed through by drift gas is located between the cross-sectional areas that are mainly passed through by ion carrier gas and the detector electrode. It is especially advantageous if at least 70% of the cross-sectional areas passed through by drift gas are located between the cross-sectional areas that are mainly passed through by ion carrier gas and the detector electrode. It has been shown that an especially effective, mobility-dependent unmixing of the analyte ions can be achieved in this way, which leads to an increase in the resolution of the IMS according to the present invention.

If measures are taken which lead to a reduction of wall reactions, it may be advantageous if the transition area and the separation area are designed such that a cross-sectional area that is mainly passed through by ion carrier gas is located on the side of the separation area facing away from the detector electrode. This may be advantageous, for example, if the flow of the ion carrier gas takes place along a Teflon-coated (polytetrafluoroethylene (PTFE) coated) wall area.

In order to prevent wall reactions, it may be advantageous as an alternative to the above embodiment, if the transition area and separation area are designed such that cross-sectional areas that are mainly passed through by ion carrier gas are surrounded at least partially by cross-sectional areas that are mainly passed through by drift gas. It is especially advantageous if a cross-sectional area that is mainly passed through by ion carrier gas includes the area of the minimum of the velocity gradient in case of a laminar flow.

Furthermore, it is advantageous for the operation of an IMS according to the present invention if at least one structural component is present that is suitable for maintaining a drift gas circulation. As a result, the IMS is, to a large extent, independent of environmental conditions, especially fluctuating ambient humidity. Its [ambient humidity] effect becomes apparent in this case only via differently conditioned ion carrier gas, whose volume percent compared to the volume percent of the drift gas can be kept small. It is especially advantageous if the drift gas circulation contains a filter for the reduction of the humidity and/or for purifying the drift gas of analytes and/or ions. The circulation operation makes possible a very economic filter operation, since a low input of substances to be filtered out is connected with long service lives of the filters.

The principle of operation of IMS according to the present invention is fundamentally determined by the radiation source used. It has been shown that it is advantageous if a radiation source is used that can convert analyte-containing air charged into the ionization chamber into ion carrier gas by ionizing the air molecules in the ionization chamber, as a result of which secondary ionizations for the formation of analyte ions are made possible. Electron sources are especially suitable for this. Especially compact and simple structures can be achieved with beta emitters.

An advantageous alternative arises if a radiation source is used that can convert analyte-containing air charged into the ionization chamber into ion carrier gas by means of the direct ionization of the analyte molecules in the ionization chamber. The use of radiation sources which comprise a source that emits electromagnetic radiation, preferably in the ultraviolet spectral range, has proven to be useful for this.

The focusing of the analyte ions according to the present invention takes place by the focusing of the ion carrier gas. This may already be influenced by a corresponding geometric design of the ionization chamber. However, it is advantageous if flow-guiding means are present, which lead to a focusing of the ion carrier gas. It is especially advantageous if the flow-guiding means comprise a diaphragm between the ionization chamber and the transition area. In an especially advantageous embodiment, this diaphragm has a slot-shaped opening.

The transition area and separation area should be embodied such that the drift gas and the ion carrier gas flow together in a laminar flow pattern behind the diaphragm in the transition area. As a result, the efficiency of the focusing of the analyte ions in certain cross-sectional areas according to the present invention is substantially increased.

The ion yield, which is significant for the sensitivity of an IMS according to the present invention, may advantageously be increased by at least surfaces which come into contact with ion carrier gas being made of a material having low surface energy. Teflon has repeatedly proven itself useful as such a material.

Another factor that substantially affects the efficiency of the IMS is the embodiment of the electric deflecting field, which is mainly affected by electrode geometry and potentials. It is advantageous if a circuit arrangement is present that holds the auxiliary electrodes and the detector electrode at the same electric potential. Furthermore, it has proven to be advantageous if a circuit is present that creates a potential distribution, in which the potential of the counterelectrode is either higher or lower than the potential of the detector electrode and that of the auxiliary electrodes. In this way, only ions of the same polarity are detected in each case. Methods of evaluation which lead to an especially high selectivity can be used if a circuit is present that creates a potential distribution, in which the potential of the counterelectrode is alternately higher and lower than the potential of the detector electrode and the potential of the auxiliary electrodes. The low deflecting voltages used according to the present invention make possible, moreover, a fast change in polarity.

Another advantage of the present invention lies in the possibility of spectral analysis by means of varying the deflecting voltage. Compared to usual methods of pattern recognition, the expense for preparing a pattern database is omitted. For carrying out a spectral analysis, it is advantageous if a circuit is present that creates a potential distribution, in which the difference in potential between the counterelectrode and at least the detector electrode varies. A complete spectrum is obtained if the difference in potential is constantly varied. Furthermore, sections from an ion spectrum can be advantageously obtained if a potential distribution is created, in which the difference in potential between the counterelectrode and at least the detector electrode jumps among a plurality of fixed values. This embodiment is especially advantageous if the presence of selected substances shall be monitored.

For a detector electrode acting selectively depending on the established potential, it is advantageous if at least one auxiliary electrode is located in front of the detector electrode, viewed in the direction of flow. An especially uniform formation of the electric deflecting field can be obtained if at least one auxiliary electrode is additionally located behind the detector electrode, viewed in the direction of flow.

Work can be performed with especially low deflecting voltages if the electrodes are arranged, such that the electric field is formed at right angles to the direction of flow. For the implementation of the principle according to the present invention, it is basically sufficient if the detector electrode consists of a single electrode. However, it is especially advantageous if the detector electrode consists of a plurality of individually wirable sectors. In this way individual sectors can be assigned to the detector electrode or to an auxiliary electrode in terms of circuit wiring. As a result, the area of the detector electrode can be varied, and the resolution, on the one hand, and the sensitivity, on the other hand, of the IMS can be influenced depending on the requirements.

It is advantageous for optimal field geometry if all electrodes are arranged in parallel to one another, especially if the detector electrode and the auxiliary electrodes lie in one plane. For field geometry, it is likewise advantageous if the counterelectrodes are arranged in one area, the detector electrode and the auxiliary electrodes are arranged in another area, and the areas of the areas have about the same size, whereby structural shapes are to be preferred, in which these areas face each other congruently.

Especially good, reproducible results are obtained if the electrodes are made of platinum or gold.

For a good separation efficiency of the IMS according to the present invention, it is advantageous if the detector electrode is more narrow perpendicular to the direction of the flow than the cross-sectional area in the transition area that is mainly passed through by ion carrier gas. In this way, falsifications of the spectrum by ions from areas near the edge areas are prevented.

In addition to the variable geometry of the detector electrode, the volume range of the IMS can be expanded by working with a variable ion carrier gas flow. The consequences of the change in flow velocity connected therewith can easily be compensated mathematically.

The present invention is explained in detail based on an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
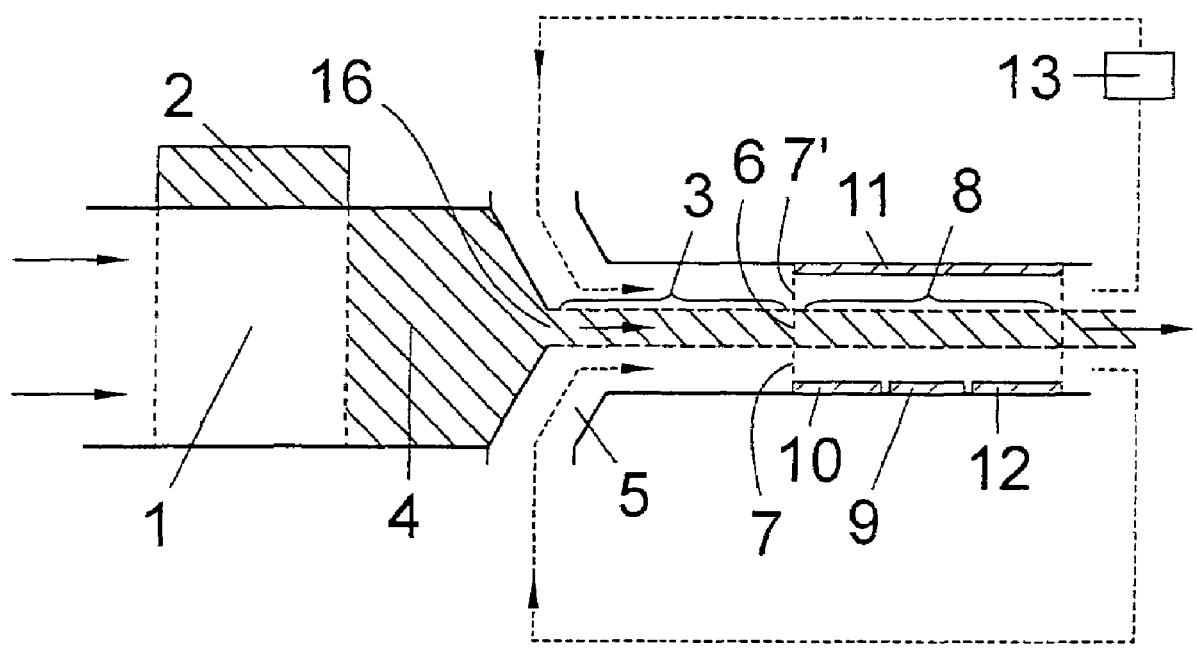
FIG. 1 is a schematic view of an ion mobility spectrometer according to the present invention.

Referring to the drawings in particular, FIG. 1 shows a schematic view of an ion mobility spectrometer according to the present invention that requires only a relatively low voltage, which lies on the order of magnitude of below 50 V, for the separation of ions and therefore can be produced in a cost-favorable manner. Arrows illustrate the occurring gas flows.

The IMS comprises an ionization chamber 1, a radiation source 2 (shown as a cross hatched region) which emits beta radiation, and a transition area 3. Under the influence of the beta radiation, analyte-containing gas flowing through the ionization chamber is ionized. As a result, in terms of the present invention, ion carrier gas 4 (shown as a cross hatched region) is formed which flows into the transition area 3. Furthermore, an almost ion-free drift gas 5 is charged into the transition area 3. The ion carrier gas 4 (shown as a cross hatched region) and drift gas 5 are charged into the transition area 3 in a way that, at least at the end of the transition area 3, a flow is established, in which cross-sectional areas 6 are mainly passed through by ion carrier gas 4 and other cross-sectional areas 7, 7' are mainly passed through by drift gas 5. A separation area 8, in which the ions are exposed to the deflecting action of an electric field, which is established between at least one detector electrode 9 with an auxiliary electrode 10 mounted next to it and a counterelectrode 11, is located behind the transition area 3 in the direction of flow. In the present example, another auxiliary electrode 12 is arranged behind the detector electrode in the direction of flow, which provides for an especially uniform field strength distribution. The almost ion-free drift gas is exhausted after passing through the separation area 8, guided via a filter 13 and charged back into the transition area. The separation efficiency of an IMS of this type that can be achieved is basically determined by the focusing of the analyte ions in a certain cross-sectional area of the flowing gas. Flow-guiding means, which are currently embodied in the form of a diaphragm 16 with a slot-shaped opening, are used for this focusing. The ion carrier gas 4 flows through the slot-shaped opening, i.e., a mechanical constriction (downstream thereof) or a focusing of the ion carrier gas occurs. After the constriction, the ion carrier gas 4 flows together with the drift gas 5 in a laminar flow pattern in the transition area.

A typical application of the present invention described here is the monitoring of ambient air. The air to be analyzed flows into the ionization chamber 1, where substances (analytes) to be detected contained in the air are ionized. The ionization by means of beta radiation (electrons) takes place in two steps. First, mainly nitrogen molecules are ionized by means of bombardment with energy-rich electrons, which can be described by the following equation:

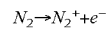

$$N_2 \rightarrow N_2^+ + e^-$$

The analytes contained in the air are hardly ionized by the electron bombardment.

Stabile $H^+(H_2O)_n$ and $O_2^-(H_2O)_n$ reactant ions as well as positive and negative analyte ion clusters are formed in secondary reactions [G. Eiceman and Z. Karpas, *Ion mobility spectrometry*, 1994]. After traversing the ionization chamber, the air contains ions and is designated as ion carrier gas.

In the transition area 3, which has a rectangular cross section in the present example, a laminar flow is formed, in which the ion carrier gas 4 is surrounded by drift gas 5 on two sides. Because of the laminar flow conditions, the laminar flow is retained in the separation area 8, such that the ions in the ion carrier gas enter the separation area 8 in a focused pattern.

The ions are deflected from the direction of flow into the direction of the electrodes by means of the electric field that is formed between the electrodes 9, 10, 11, 12 arranged opposite one another. For the detection of positive ions, the auxiliary electrodes 10, 12 and the detector electrode 9 are at a lower potential than the counterelectrode 11 (positive mode). The auxiliary electrodes 10, 12 and the detector electrode 9 lie ideally in one plane and at the same potential. Thus, positive ions are deflected in the direction of the auxiliary electrodes 10, 12 and the detector electrode 9. Only ions with a certain mobility reach the detector electrode 9 at a corresponding deflecting voltage, since the flow velocity and the deflecting velocity match in the correct ratio only for these ions. An ion flow is formed between the detector electrode 9 and the counterelectrode 11 that correlates with the concentration of these ions and thus with the concentration of the corresponding analytes in the ambient air.

In order to guarantee the development of a field that is as uniform as possible, the counterelectrode 11, in terms of surface measure, is located congruently in parallel to the auxiliary electrodes 10, 12 and the detector electrode 9, which lie in one plane. An ion spectrum can be obtained by changing the deflecting voltage. Because of the focusing and spectral analysis, the system has an improved separation efficiency compared to other systems (e.g., ChemPro 100 of the firm of Environics). For the detection of relatively charged ions, the potential conditions can easily be reversed (negative mode). Because of the low deflecting voltages, switching between positive mode and negative mode in the range from 1 Hz to 5 Hz is possible.

After passing through the separation area 8, the drift gas 5 is guided via a filter 13 and charged back into the transition area 3. Humidity, analytes and other impurities are consequently removed from the drift gas, i.e., the separation of ions takes place in dry and clean air almost independently of the ambient humidity.

A minimal media requirement results from a reduction of the dimensions of the system. The simple method of construction and low production costs connected therewith are especially advantageous. The volume range of the system can be increased simply by changing the gas flows both of the ion carrier gas and of the drift gas and by mathematical consideration of the changed flight ranges.

Figure 2:
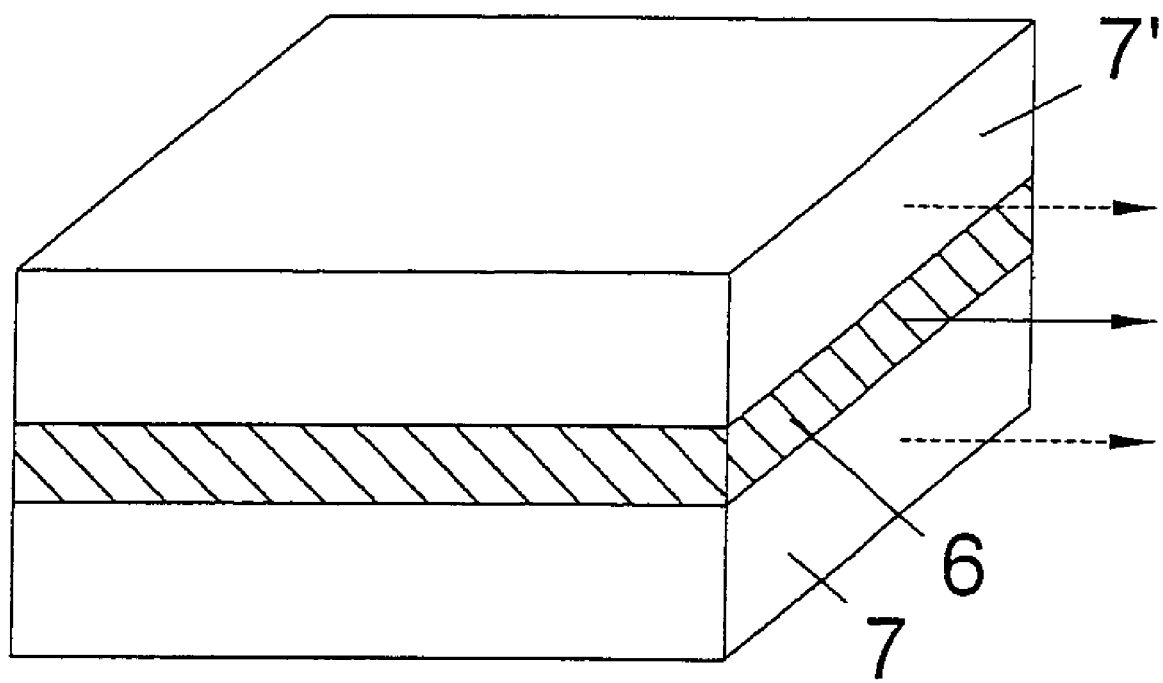
FIG. 2 is a schematic view of the flow conditions in a section of the transition area.

FIG. 2 shows a schematic view of the flow conditions in a section of the transition area. In the transition area, which has a rectangular cross section in the present example, a laminar flow is formed, in which the ion carrier gas is surrounded by drift gas on two sides. Because of the laminar flow conditions, the laminar flow is retained in the separation area, so that the ions in the ion carrier gas enter the separation area in a focused pattern.

For the principle according to the present invention it is important that these flow conditions prevail at least at the end of the transition area. An effective focusing of the ions takes place upon their entry into the separation area, if it is achieved that, at least at the end of the transition area, a flow is established, in which cross-sectional area 6 (shown as a cross hatched region) is mainly passed through by ion carrier gas and other cross-sectional areas 7, 7' are mainly passed through by drift gas.

Figure 3:
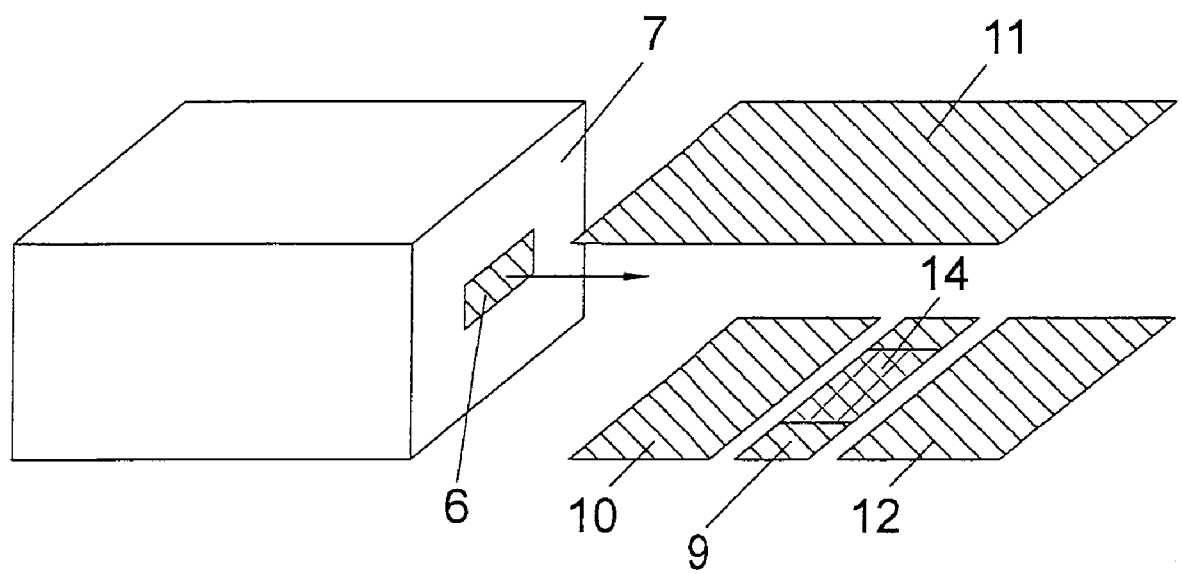
FIG. 3 is a schematic view showing another advantageous embodiment of the flow conditions in a section of the transition area.

FIG. 3 shows another advantageous embodiment of the flow conditions in a section of the transition area. In this example, a cross-sectional area 6 (shown as a cross hatched region) that is mainly passed through by ion carrier gas is located in the middle of the transition area. It is surrounded by a cross-sectional area 7 that is mainly passed through by drift gas. As a result, it is achieved that the cross-sectional area 6 that is mainly passed through by ion carrier gas surrounds the area of the minimum of the velocity gradient of the gas flow in case of a laminar flow. The arrangement of the electrodes corresponds to the previous example. The detector electrode 9 and the auxiliary electrodes 10, 12 are located in one plane opposite the counterelectrode 11. The special flow geometry results in a constricted target area 14, in which the analyte ions to be detected reach the detector electrode.

Figure 4:
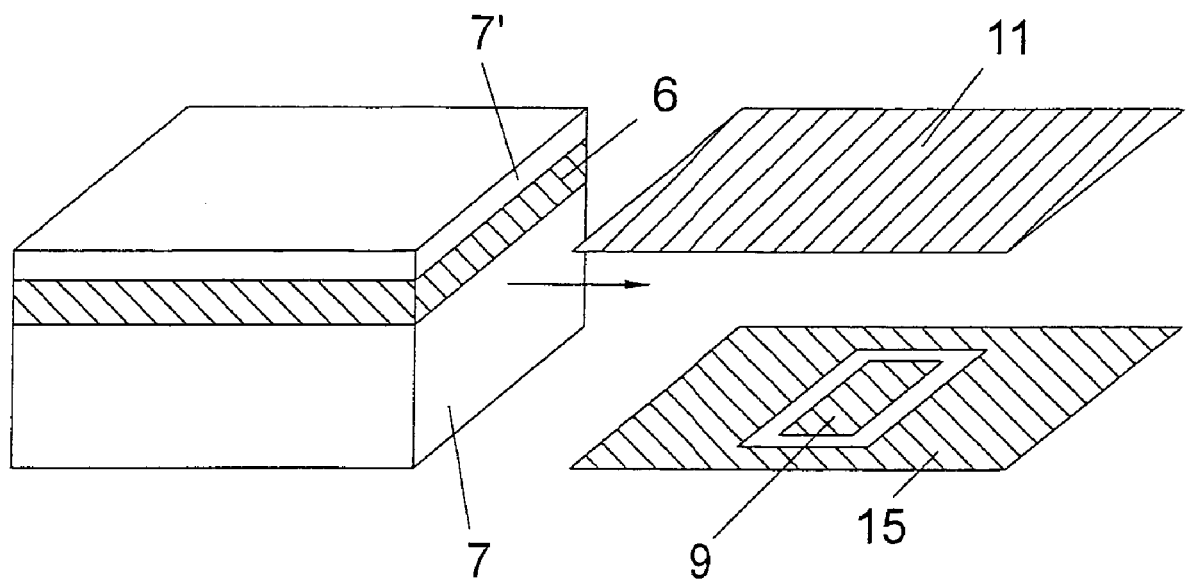
FIG. 4 is a schematic view showing another advantageous embodiment of the flow conditions in a section of the transition area in combination with a modified electrode array.

FIG. 4 shows another advantageous embodiment of the flow conditions in a section of the transition area in combination with a modified electrode arrangement. The transition area and the separation area are embodied, such that at least 70% of the cross-sectional areas 7, 7' that are mainly passed through by drift gas are located between a cross-sectional area 6 (shown as a cross hatched region) that is mainly passed through by ion carrier gas and the detector electrode. This is achieved by an asymmetric structure of the laminar flow. The lower cross-sectional area 7 passed through by drift gas is considerably more expanded than the cross-sectional area 7' that is formed in the form of a thin protective flow between the ion carrier gas and the wall or counterelectrode 11. It has been shown that especially high separation efficiencies can be achieved with asymmetric flow geometries of this type. In order to rule out effects due to flow inhomogeneities at the edges of the flow path, a detector electrode 9 was selected that is more narrow perpendicular to the direction of flow than the cross-sectional area 6 (shown as a cross hatched region) in the transition area that is mainly passed through by ion carrier gas. This detector electrode is preferably surrounded by a ring-shaped auxiliary electrode 15.

While specific embodiments of the invention have been shown and described in detail to illustrate the application of the principles of the invention, it will be understood that the invention may be embodied otherwise without departing from such principles.

What is claimed is:

1. An ion mobility spectrometer comprising:
   an ionization chamber, which can be passed through by an analyte-containing gas;
   a radiation source directing ionizing radiation, which is suitable for at least partially ionizing the analyte-containing gas, to enter said ionization chamber;
   a transition area, into which the at least partially ionized gas as ion carrier gas and an almost ion-free gas as said drift gas are charged such that at least at the end of said transition area a flow is established including a cross-sectional area mainly passed through by said ion carrier gas and other cross-sectional areas mainly passed through by said drift gas;
   a separation area lying in the direction of flow downstream of said transition area, said separation area having a cross-sectional area mainly passed through by said ion carrier gas and other cross-sectional areas mainly passed through by said drift gas, whereby said drift gas and said ion carrier gas flow unidirectionally, wherein said cross-sectional area mainly passed through by said ion carrier gas is smaller at least in one dimension than said cross-sectional areas that are mainly passed through by said drift gas; and
   electrodes including a detector electrode, an auxiliary electrode and a counterelectrode, said electrodes being arranged in said separation area whereby an electric field can be formed between them, said electric field having at least one field component that does not run parallel to the direction of flow in said separation area, whereby at least one said other cross-sectional areas that are mainly passed through by said drift gas is located between said cross-sectional area that is mainly passed through by said ion carrier gas and said detector electrode.

2. An ion mobility spectrometer in accordance with claim 1, wherein said cross-sectional area that is mainly passed through by said ion carrier gas is smaller in two dimensions than said cross-sectional areas that are mainly passed through by said drift gas.

3. An ion mobility spectrometer in accordance with claim 1, wherein said cross-sectional area that is mainly passed through by said ion carrier gas has a smaller dimensions at least in the direction of the electric field than said cross-sectional areas that are mainly passed through by said drift gas.

4. An ion mobility spectrometer in accordance with claim 1, wherein said cross-sectional area that is mainly passed through by said ion carrier gas is smaller by at least a factor of 10 at least in one dimension than said cross-sectional areas that are mainly passed through by said drift gas.

5. An ion mobility spectrometer in accordance with claim 1, wherein said cross-sectional area that is mainly passed through by said ion carrier gas is smaller by at least a factor of 50 at least in one dimension than said cross-sectional areas that are mainly passed through by said drift gas.

6. An ion mobility spectrometer in accordance with claim 1, wherein said transition area and said separation area are embodied, such that a main part of said cross-sectional areas that are mainly passed through by said drift gas is located between said cross-sectional area that is mainly passed through by said ion carrier gas and said detector electrode.

7. An ion mobility spectrometer in accordance with claim 1, wherein said transition area and said separation area are embodied such that at least 70% of said cross-sectional areas that are mainly passed through by said drift gas are located between said cross-sectional area that is mainly passed through by said ion carrier gas and said detector electrode.

8. An ion mobility spectrometer in accordance with claim 6, wherein said transition area and said separation area are embodied such that said cross-sectional area that is mainly passed through by said ion carrier gas is located on a side of said separation area facing away from said detector electrode.

9. An ion mobility spectrometer in accordance with claim 6, wherein said transition area and said separation area are embodied such that said cross-sectional area that is mainly passed through by said ion carrier gas is at least partially surrounded by said cross-sectional areas that are mainly passed through by said drift gas.

10. An ion mobility spectrometer in accordance with claim 9, wherein said transition area and said separation area are embodied such that said cross-sectional area that is mainly passed through by said ion carrier gas includes the area of the minimum of the velocity gradient in case of a laminar flow.

11. An ion mobility spectrometer in accordance with claim 1, further comprising drift gas circulation means for maintaining a drift gas circulation.

12. An ion mobility spectrometer in accordance with claim 11, wherein said drift gas circulation means includes a filter for reducing humidity and/or for purifying the drift gas of analytes and/or ions.

13. An ion mobility spectrometer in accordance with claim 1, wherein said radiation source can convert analyte-containing air or gas charged into said ionization chamber into ion carrier gas by ionizing the air or gas molecules in said ionization chamber, as a result of which the formation of analyte ions is made possible by means of secondary ionizations.

14. An ion mobility spectrometer in accordance with claim 1, wherein said radiation source can convert analyte-containing air or gas charged into said ionization chamber into ion carrier gas by direct ionization of the analyte molecules in said ionization chamber.

15. An ion mobility spectrometer in accordance with claim 13, wherein said radiation source comprises an electron source including a beta emitter.

16. An ion mobility spectrometer in accordance with claim 14, wherein said radiation source comprises a source that emits electromagnetic radiation including radiation in the ultraviolet spectral range.

17. An ion mobility spectrometer in accordance with claim 1, further comprising flow-guiding means that lead to a focusing of said ion carrier gas.

18. An ion mobility spectrometer in accordance with claim 17, wherein said flow-guiding means comprises a diaphragm between said ionization chamber and said transition area.

19. An ion mobility spectrometer in accordance with claim 18, wherein said diaphragm has a slot-shaped opening.

20. An ion mobility spectrometer in accordance with claim 1, wherein said flow-guiding means comprises a diaphragm between said ionization chamber and said transition area and said transition area and said separation area are embodied, such that said drift gas and said ion carrier gas flow together in a laminar flow pattern in said transition area behind said diaphragm.

21. An ion mobility spectrometer in accordance with claim 1, wherein at least surfaces that come into contact with ion carrier gas are made of a material having low surface energy.

22. An ion mobility spectrometer in accordance with claim 1, wherein surfaces that come into contact with ion carrier gas are made of Teflon.

23. An ion mobility spectrometer in accordance with claim 1, wherein a circuit arrangement is present that holds said auxiliary electrode and said detector electrode at the same electric potential.

24. An ion mobility spectrometer in accordance with claim 1, further comprising a circuit that creates a potential distribution, in which the potential of said counterelectrode is higher than the potential of said detector electrode and that of said auxiliary electrode.

25. An ion mobility spectrometer in accordance with claim 1, further comprising a circuit that creates a potential distribution, in which the potential of said counterelectrode is lower than the potential of said detector electrode and that of said auxiliary electrode.

26. An ion mobility spectrometer in accordance with claim 1, further comprising a circuit that creates a potential distribution, in which the potential of said counterelectrode is alternately higher and lower than the potential of said detector electrode and the potential of said auxiliary electrode.

27. An ion mobility spectrometer in accordance with claim 1, further comprising a circuit that creates a potential distribution, in which the difference in potential between said counterelectrode and at least said detector electrode varies.

28. An ion mobility spectrometer in accordance with claim 27, further comprising a circuit that creates a potential distribution, in which the difference in potential between said counterelectrode and at least said detector electrode varies constantly.

29. An ion mobility spectrometer in accordance with claim 27, further comprising a circuit that creates a potential distribution, in which the difference in potential between said counterelectrode and at least said detector electrode jumps among a plurality of fixed values.

30. An ion mobility spectrometer in accordance with claim 1, wherein at least one said auxiliary electrode is located upstream of said detector electrode, as viewed in the direction of flow.

31. An ion mobility spectrometer in accordance with claim 30, wherein at least one said auxiliary electrode is located downstream of said detector electrode, as viewed in the direction of flow.

32. An ion mobility spectrometer in accordance with claim 1, wherein the electrodes are arranged, such that the electric field is formed at right angles to the direction of flow.

33. An ion mobility spectrometer in accordance with claim 1, wherein said detector electrode consists of a single electrode.

34. An ion mobility spectrometer in accordance with claim 1, wherein said detector electrode consists of a plurality of individually wirable sectors.

35. An ion mobility spectrometer in accordance with claim 1, wherein said electrodes are arranged in parallel to one another.

36. An ion mobility spectrometer in accordance with claim 1, wherein said auxiliary electrode and said detector electrode are arranged in one plane.

37. An ion mobility spectrometer in accordance with claim 1, wherein said counterelectrode is arranged in one area, said detector electrode and said auxiliary electrode are arranged in another area, and the area of said one area and said another area have the same size.

38. An ion mobility spectrometer in accordance with claim 1, wherein an area in which said counterelectrode is arranged and an area in which said detector electrode and said auxiliary electrode are arranged, face each other congruently.

39. An ion mobility spectrometer in accordance with claim 1, wherein said electrodes are made of platinum or gold.

40. An ion mobility spectrometer in accordance with claim 1, wherein said detector electrode is more narrow perpendicular to the direction of flow than a cross-sectional area in said transition area, which is mainly passed through by said ion carrier gas.

41. An ion mobility spectrometer in accordance with claim 1, wherein the ion carrier gas flow is variable.

* * * * *